United States Patent
Jach et al.

(10) Patent No.: US 6,261,429 B1
(45) Date of Patent: Jul. 17, 2001

(54) SENSOR ELEMENT

(75) Inventors: Olaf Jach, Boeblingen; Lothar Diehl, Stuttgart, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/239,280

(22) Filed: Jan. 29, 1999

(30) Foreign Application Priority Data

Jan. 30, 1998 (DE) .............................. 198 03 562

(51) Int. Cl.⁷ .................................................. G01N 27/26
(52) U.S. Cl. ..................... 204/427; 204/408; 204/426; 204/429
(58) Field of Search .................. 204/408, 421–429

(56) References Cited

U.S. PATENT DOCUMENTS

| | | |
|---|---|---|
| 4,300,990 | 11/1981 | Maurer . |
| 4,861,456 * | 8/1989 | Mase et al. ............... 204/426 |
| 5,529,677 * | 6/1996 | Schneider et al. ........ 204/426 |
| 5,658,445 * | 8/1997 | Hafele et al. ............. 204/425 |
| 5,895,591 * | 4/1999 | Kojima et al. ............ 204/426 |
| 5,902,470 * | 5/1999 | Schneider et al. ........ 204/427 |
| 5,985,118 * | 11/1999 | Makino et al. ............ 204/426 |

FOREIGN PATENT DOCUMENTS

| | | |
|---|---|---|
| 196 09 323 A1 | 9/1997 | (DE) . |
| 0 343 533 | 11/1989 | (EP) . |

* cited by examiner

*Primary Examiner*—T. Tung
(74) *Attorney, Agent, or Firm*—Kenyon & Kenyon

(57) ABSTRACT

A sensor element for an electrochemical sensor, in particular for determining the oxygen content in exhaust gases of an internal combustion engine. The sensor element has at least one measuring electrode exposed to a measuring gas, at least one reference electrode exposed to a reference gas, at least one heating device having one heating conductor and two heating conductor leads, and a reference gas channel. The heating conductor has at least two heating circuit trace segments outside the vertical projection of the reference gas channel, the two heating circuit trace segments being connected by a connecting segment routed over the reference gas channel. The circuit trace cross section of the connecting segment is larger than the cross section of one of the heating circuit trace segments.

8 Claims, 1 Drawing Sheet

SENSOR ELEMENT

FIELD OF THE INVENTION

The present invention relates to a sensor element for an electrochemical sensor for determining oxygen content in exhaust gases from an internal combustion engine.

BACKGROUND OF THE INVENTION

Sensor elements for determining oxygen content are composed of ceramic foils made of, for example, stabilized $ZrO_2$, which are imprinted with electrodes having electrode leads and a heating device having a heating conductor and heating conductor leads, and which, after being laminated together and then sintered, yield a planar sensor element. In the case of electrochemical sensors, the heating device is embedded between two electrically insulating layers, for example, made of $Al_2O_3$, which, in turn, are arranged, in each case, with regard to the adjoining oxygen-ion-conducting ceramic sheets.

In electrochemical sensor elements that operate using a reference gas, an electrode is disposed in a reference gas channel, which extends, for example, in the longitudinal direction of the sensor element and is in contact with ambient air. This reference gas channel runs in a plane of the layer between the reference electrode and the heating device.

In those areas in which the heating conductor spans the reference gas channel, there is poor heat dissipation for the heat generated, so that in this area it is possible that the heating conductor may overheat. In addition, the poor heat conduction in the area of the reference gas channel means that it is only possible to heat the sensor elements to their operating temperature using increased heating energy or after a correspondingly long warm-up period.

German Patent No. 196 09 323 describes that improved heat conduction may be achieved by arranging the heat conductor of the heating device outside the projection of the reference gas channel. For this purpose, the reference gas channel has been designed in two parts, in the area of the electrodes and the heat conductor.

SUMMARY OF THE INVENTION

The sensor element according to the present invention has the advantage that the heat transfer from the heating device to the sensitive, electrode-bearing area of the sensor element is markedly improved. An overheating of the heating conductor in the area of the reference gas channel is avoided with the result that long-term stability of the heating device and thus of the sensor element is increased.

Loop-shaped extension segments of the heating circuit trace segments, that are designed on a narrow end of a measuring gas side on a large surface, provide a resistance relationship of the heating conductor leads and the heating conductor shifted to the advantage of the heating conductor. In this way, it is also possible to more quickly heat up the sensor element (quick-start heater). Moreover, as a result of the improved heating of the narrow end of the measuring gas side, the resistance to thermal shock of the sensor element is increased.

In addition, by heating the electrode leads, a capacitive and resistance coupling of the electrode leads increases, which ultimately leads to a distortion of the measuring signal as a result of over and undershooting in response to changes of concentration in the measuring gas. By moving the heat generation to the tip of the sensor element, i.e., to the sensitive area of the electrodes, the capacitive and resistance coupling of the leads in the sensor element is reduced.

As a result of the tapering and expanding configuration of the transitions from the heating conductor leads to the heating circuit trace segments and from the heating circuit trace segments to a connecting segment, the danger of leakage currents in response to local overheating is reduced. Leakage currents arise as a result of the formation of a current path between the heating device and an electrode, resulting ultimately in distorting the measuring signal received from the electrodes. By enlarging the insulated areas between the meandering branches, the high potential differences in areas between the meandering branches are at the same time attenuated.

Widening the reference gas channel inside the area that is not covered by the heating conductor also has the advantage that the reference electrode may be enlarged accordingly and that an improved reference gas exchange is possible.

SUMMARY OF THE INVENTION

Figure 1:
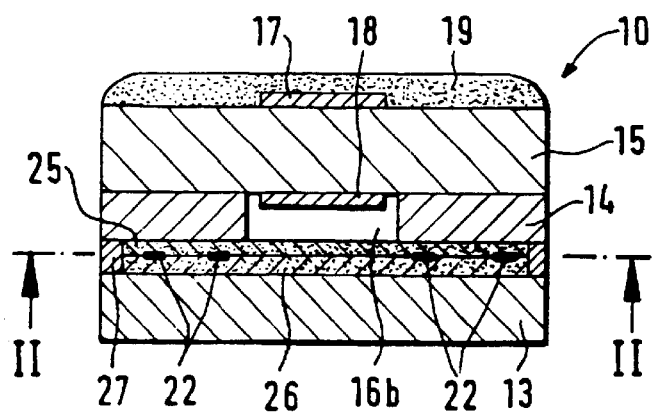
FIG. 1 shows a cross section of an exemplary embodiment of a sensor element according to the present invention.

FIG. 1 depicts a cross section of a sensor element 10 of an electrochemical sensor. Sensor element 10, according to FIG. 2, has an end segment 11 on the connection side and an end segment 12 on the measuring gas side, and has a planar layer construction composed of a plurality of ceramic foils. In the present exemplary embodiment, sensor element 10 has a covering foil 13, a reference gas channel foil 14, and a sensor foil 15. Ceramic foils 13, 14, 15, are designed to be rectangular, and, in each case, they have two large surfaces opposite each other. Ceramic foils 13, 14, and 15, are oxygen-ion-conductive and are made, for example, of stabilized $ZrO_2$.

Figure 2:
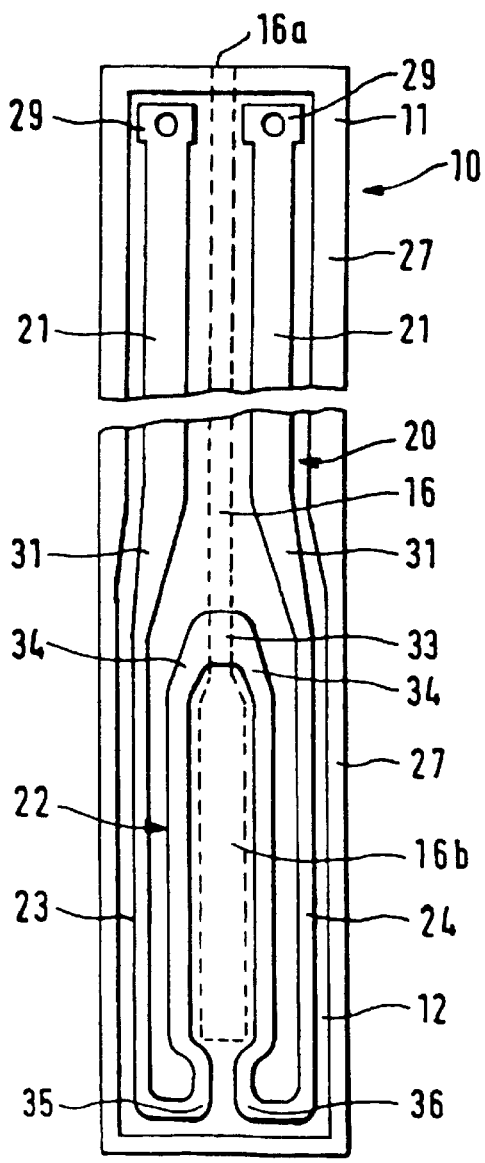
FIG. 2 shows a longitudinal segment of the sensor element shown in FIG. 1 at the line II—II.

In reference gas channel foil 14, a hollow space is configured as reference gas channel 16. Reference gas channel 16 extends from end segment 11 on the connection side, at which it exits on the narrow end side having an opening 16a, to end segment 12 on the measuring gas side, where it is closed and forms a reference gas chamber 16b. Reference gas chamber 16b widens in comparison to reference gas channel 16 (FIG. 2).

On the outer large surface, sensor foil 15 supports a measuring electrode 17 and, on the opposite inner large surface, supports a reference electrode 18 pointing to reference gas chamber 16b. Measuring electrode 17 is covered with a porous protective layer 19 and is exposed to the measuring gas (FIG. 1).

Between covering foil 13 and reference gas channel foil 14, an electrical heating device 20 is arranged. From the top view in accordance with FIG. 2, the design of heating device 20, running in the plane of the layer, and that of reference gas channel 16 having reference gas chamber 16b are visible. Heating device 20, situated parallel to the large surfaces of ceramic foils 13, 14, and 15, has two heating conductor leads 21, and on end segment 12 on the measuring gas side of sensor element 10, a meanderous-shaped heating conductor 22 composed of a left heating circuit trace segment 23 and a right heating circuit trace segment 24. On end segment 11 on the connection side, both heating conductor leads 21 have contact locations 29 for through-contacts that are not depicted further, by means of which heating conductor leads 21 are routed to the outer large surface of sensor element 10.

For the purpose of electrical insulation from the adjoining ceramic foils 13 and 14, heating device 20 according to FIG. 1 is embedded in two insulating layers 25, 26 made of, for example, $Al_2O_3$. For the purpose of sealing insulating layers 25, 26, a sealing frame 27 composed of, for example, the material of the adjoining ceramic foils 13, 14 is placed around the heating device.

In the direction of end segment 12 on the measuring gas side at the end of heating conductor leads 21, there is formed a circuit trace segment 31, in which heating conductor leads 21 continually taper towards the narrower width of heating conductor 22. In the longitudinal direction, at approximately the height of circuit trace segment 31, heating conductor 22 has a connecting segment 33, to which heating conductor 22 is routed, outside reference gas chamber 16b, over reference gas channel 16. Connecting segment 33, in comparison to heating circuit trace segments 23, 24, is designed to be wider, and it has, for example, the width of heating conductor leads 21. As a result, connecting segment 33 has a smaller ohmic resistance than a comparable area of heating circuit trace segments 23, 24. Via further circuit trace segments 34, narrower heating circuit trace segments 23, 24 are routed to wider connecting segment 33, in a configuration similar to that of circuit trace segments 31. As a result of the bent designs of the meandering branches having circuit trace segments 31, 34, there arise, in the areas having high potential difference, greater clearances between the meandering branches and greater cross sections of the leads. As a result, these high potential differences in areas are attenuated, thus lessening the danger of leakage currents in response to local overheating.

On end segment 15 on the measuring gas side, both heating circuit trace segments 23, 24 have a left loop-shaped circuit trace segment 35 and a right loop-shaped circuit trace segment 36, respectively. Heating conductor 22 is lengthened by an extension segment, which is defined two loop-shaped circuit trace segments 35, 36, thus achieving a high heat productivity in front end segment 12 on the measuring gas side of sensor element 10. As a result of the improved heating of the end side of sensor element 10, thermal shock cracks arising from the tensile stresses of the cold surface in response to turning on heating device 20, are avoided. In addition, since reference gas chamber 16b is essentially surrounded at its end by heating conductor 22, the heat transfer to adjoining ceramic foils 14 is improved.

The heating conductor 22 includes heating circuit trace segments 23, 24 which are situated outside the vertical projection of reference gas chamber 16b. A circuit trace segment, in the form of connecting segment 33, is routed over narrow reference gas channel 16, the circuit trace segment having a larger cross section than the cross section of heating conductor 22 and the largest cross section of one of heating circuit trace segments 23, 24. In this way, it is assured that heating conductor 22 having heating circuit trace segments 23, 24 is squeezed between adjoining foils 13, 14, thus improving heat transfer, in particular, via reference channel foil 14 to sensor foil 15. Reference gas channel 16 exercises an extremely slight dampening of the heat transfer only in the area of connecting segment 33, which in addition has no essential heating function.

The heater design of the present invention is not limited to sensor element 10 as described. It is just as applicable in the case of other sensor elements that have a hollow space between the heating device and the sensitive area.

What is claimed is:

1. A sensor element for an electrochemical sensor for determining oxygen content in exhaust gases of an internal combustion engine, comprising:

at least one measuring electrode exposed to a measuring gas;

at least one reference electrode exposed to a reference gas; and at least one heating device including a heating conductor and heating conductor leads, the heating conductor having at least two first heating circuit trace segments, each of the at least two first heating circuit trace segments being disposed outside a vertical projection of a reference gas channel, each of the at least two first heating circuit trace segments being conductively connected over the reference gas channel by a connecting segment having a larger circuit trace cross section than a cross section of each of the at least two first heating circuit trace segments, the connecting segment spanning the reference gas channel, the reference gas channel conveying the reference gas to the at least one reference electrode.

2. The sensor element according to claim 1, wherein the reference gas channel widens forming a reference gas chamber in an area near the at least one reference electrode, and the connecting segment is routed outside the vertical projection of the reference gas chamber over a narrower portion of the reference gas channel.

3. The sensor element according to claim 1, wherein at least one of the at least two first heating circuit trace segments has a turning on a measuring gas side, the turning defining an extension segment.

4. The sensor element according to claim 3, wherein each extension segment has a loop shape substantially encircling an end of the measuring gas side of the reference gas channel, each extension segment being formed at the at least two first heating circuit trace segments.

5. The sensor according to claim 1, further comprising:

a second circuit trace segment formed between each of the at least two first heating circuit trace segments and the connecting segment, a width of the at least two first heating circuit trace segments increasing towards the connecting segment, the first heating circuit trace segments being conductively connected over the reference gas channel by the connecting segment via the second circuit trace segments.

6. The sensor element according to claim 5, further comprising:

a third circuit trace segment formed between the heating conductor leads and the at least two first heating circuit trace segments, the third circuit trace segment being adjacent, in relation to a longitudinal extension of a large surface of the sensor element, to the second circuit trace segment, the third circuit trace segment being at approximately the same level as the second circuit trace segment.

7. The sensor according to claim 1, further comprising:

a third circuit trace segment formed between the heating conductor leads and the at least two first heating circuit trace segments, each of the heating conductor leads having a width tapering towards the at least two first heating circuit trace segments.

8. The sensor element according to claim 1, wherein the at least two first heating circuit trace segments are arranged symmetrically in a plane of a large surface of the sensor element.

* * * * *